United States Patent
Du

(10) Patent No.: US 9,119,771 B2
(45) Date of Patent: *Sep. 1, 2015

(54) NON-SEDATING ANTIHISTAMINE INJECTION FORMULATIONS AND METHODS OF USE THEREOF

(75) Inventor: Jie Du, Lansdale, PA (US)

(73) Assignee: JDP THERAPEUTICS, INC., Lansdale, PA (US)

(*) Notice: Subject to any disclaimer, the term of this patent is extended or adjusted under 35 U.S.C. 154(b) by 168 days.

This patent is subject to a terminal disclaimer.

(21) Appl. No.: 13/559,954

(22) Filed: Jul. 27, 2012

(65) Prior Publication Data

US 2012/0289489 A1    Nov. 15, 2012

Related U.S. Application Data

(63) Continuation of application No. 12/704,089, filed on Feb. 11, 2010, now Pat. No. 8,263,581.

(60) Provisional application No. 61/248,441, filed on Oct. 3, 2009, provisional application No. 61/222,951, filed on Jul. 3, 2009.

(51) Int. Cl.
| | |
|---|---|
| A61K 31/56 | (2006.01) |
| A61K 31/4965 | (2006.01) |
| A61K 9/00 | (2006.01) |
| A61K 31/137 | (2006.01) |
| A61K 31/341 | (2006.01) |
| A61K 31/4164 | (2006.01) |
| A61K 31/495 | (2006.01) |
| A61K 31/573 | (2006.01) |
| A61K 31/445 | (2006.01) |
| A61K 31/4545 | (2006.01) |
| A61K 45/06 | (2006.01) |

(52) U.S. Cl.
CPC ............. *A61K 9/0019* (2013.01); *A61K 31/137* (2013.01); *A61K 31/341* (2013.01); *A61K 31/4164* (2013.01); *A61K 31/445* (2013.01); *A61K 31/4545* (2013.01); *A61K 31/495* (2013.01); *A61K 31/573* (2013.01); *A61K 45/06* (2013.01)

(58) Field of Classification Search
None
See application file for complete search history.

(56) References Cited

U.S. PATENT DOCUMENTS

| | | |
|---|---|---|
| 4,117,141 A | 9/1978 | Michaeli |
| 4,434,237 A | 2/1984 | Dinarello |
| 4,525,358 A | 6/1985 | Baltes et al. |
| 4,826,689 A | 5/1989 | Violanto et al. |
| 5,276,044 A | 1/1994 | Ambrus et al. |
| 5,419,898 A | 5/1995 | Ikejiri et al. |
| 5,492,935 A | 2/1996 | Yu et al. |
| 5,627,183 A | 5/1997 | Gray |
| 5,627,284 A | 5/1997 | Takase et al. |
| 5,698,558 A | 12/1997 | Gray |
| 6,258,816 B1 | 7/2001 | Singh et al. |
| 6,319,927 B1 | 11/2001 | Martin |
| 6,384,038 B1 | 5/2002 | Rubin |
| 6,432,961 B1 | 8/2002 | Uylenbroeck et al. |
| 6,451,815 B1 | 9/2002 | Hwang et al. |
| 6,509,014 B1 | 1/2003 | De Lacharriere et al. |
| 6,537,573 B2 | 3/2003 | Johnson et al. |
| 6,660,301 B1 | 12/2003 | Vogel et al. |
| 6,670,384 B2 | 12/2003 | Bandypadhyay et al. |
| 6,720,001 B2 | 4/2004 | Chen et al. |
| 6,790,847 B2 | 9/2004 | Walch |
| 6,824,786 B2 | 11/2004 | Yu et al. |
| 7,026,360 B1 | 4/2006 | Festo |
| 7,115,563 B2 | 10/2006 | Younis et al. |
| 7,338,657 B2 | 3/2008 | Vogel et al. |
| 2001/0038863 A1 | 11/2001 | Jaenicke et al. |
| 2002/0012700 A1 | 1/2002 | Johnson et al. |
| 2002/0031558 A1 | 3/2002 | Yoo |
| 2002/0048596 A1 | 4/2002 | Cevc |
| 2002/0164374 A1 | 11/2002 | Jackson et al. |
| 2002/0169190 A1 | 11/2002 | Bandyopadhyay et al. |
| 2003/0068375 A1 | 4/2003 | Wright et al. |
| 2003/0108496 A1 | 6/2003 | Yu et al. |
| 2003/0134810 A1 | 7/2003 | Springate et al. |

(Continued)

FOREIGN PATENT DOCUMENTS

| | | |
|---|---|---|
| EP | 1005865 A1 | 6/2000 |
| EP | 1109557 B1 | 11/2002 |

(Continued)

OTHER PUBLICATIONS

Allegra (fexofenadine hydrochloride) tablets; product label; Allegra ODT manufactured for Sanofi-Aventis U.S. LLC; 19 pages; (2007).

(Continued)

*Primary Examiner* — Craig Ricci

(74) *Attorney, Agent, or Firm* — Cantor Colburn LLP

(57) ABSTRACT

Described herein are injectable compositions containing non-sedating or second and third generation antihistamines such as cetirizine/levocetirizine and methods of use thereof. Specifically, methods of treating acute allergic reactions including anaphylaxis with the compositions are disclosed. In certain embodiments, the injectable compositions are bioequivalent to currently marketed oral dosage forms. In other embodiments, the non-sedating or second and third generation antihistamine injectable formulations are therapeutically equivalent to diphenhydramine injectable formulations and/or are more effective than placebo. In other embodiments, a non-sedating antihistamine injectable composition is delivered by an autoinjector.

18 Claims, No Drawings

(56) References Cited

U.S. PATENT DOCUMENTS

| | | |
|---|---|---|
| 2003/0134811 A1 | 7/2003 | Jackson et al. |
| 2003/0143184 A1 | 7/2003 | Seo et al. |
| 2003/0144336 A1 | 7/2003 | Chen et al. |
| 2003/0211083 A1 | 11/2003 | Vogel et al. |
| 2004/0077540 A1 | 4/2004 | Quay |
| 2004/0142852 A1 | 7/2004 | Younis et al. |
| 2004/0185145 A1 | 9/2004 | Ehrman et al. |
| 2004/0197324 A1 | 10/2004 | Liu et al. |
| 2004/0203145 A1 | 10/2004 | Zamore et al. |
| 2004/0228831 A1 | 11/2004 | Belinka, Jr. et al. |
| 2004/0247660 A1 | 12/2004 | Singh |
| 2004/0268425 A1 | 12/2004 | Bookbinder et al. |
| 2005/0031667 A1 | 2/2005 | Patel et al. |
| 2005/0031713 A1 | 2/2005 | Ehrich et al. |
| 2005/0032173 A1 | 2/2005 | Rojas et al. |
| 2005/0042293 A1 | 2/2005 | Jackson et al. |
| 2005/0147607 A1 | 7/2005 | Reed |
| 2005/0158408 A1 | 7/2005 | Yoo |
| 2005/0202090 A1 | 9/2005 | Clarke |
| 2005/0208134 A1 | 9/2005 | Magdassi et al. |
| 2005/0260186 A1 | 11/2005 | Bookbinder et al. |
| 2005/0282879 A1 | 12/2005 | Salehani |
| 2006/0002963 A1 | 1/2006 | Rabinovich-Guilatt et al. |
| 2006/0079558 A1 | 4/2006 | Aberg et al. |
| 2006/0079559 A1 | 4/2006 | Aberg et al. |
| 2006/0079846 A1 | 4/2006 | Williams |
| 2006/0084683 A1 | 4/2006 | Uylenbroeck et al. |
| 2006/0095075 A1 | 5/2006 | Burkinshaw et al. |
| 2006/0106364 A1 | 5/2006 | Whitlock et al. |
| 2006/0148903 A1 | 7/2006 | Burch et al. |
| 2006/0210604 A1 | 9/2006 | Dadey et al. |
| 2006/0211754 A1 | 9/2006 | Yu et al. |
| 2006/0216363 A1 | 9/2006 | Liu et al. |
| 2006/0241017 A1 | 10/2006 | Chandran |
| 2006/0247258 A1 | 11/2006 | Revirron |
| 2006/0287244 A1 | 12/2006 | Chandran |
| 2007/0014843 A1 | 1/2007 | Dobak |
| 2007/0020196 A1 | 1/2007 | Pipkin et al. |
| 2007/0021326 A1 | 1/2007 | Hamid et al. |
| 2007/0026058 A1 | 2/2007 | Pereswetoff-Morath et al. |
| 2007/0053900 A1 | 3/2007 | Liu et al. |
| 2007/0128276 A1 | 6/2007 | Jain et al. |
| 2007/0166368 A1 | 7/2007 | Singh |
| 2007/0191781 A1 | 8/2007 | Richards et al. |
| 2007/0203247 A1 | 8/2007 | Phillips et al. |
| 2007/0213660 A1 | 9/2007 | Richards et al. |
| 2007/0219498 A1 | 9/2007 | Malone et al. |
| 2007/0264349 A1 | 11/2007 | Lee et al. |
| 2007/0281947 A1 | 12/2007 | Matsumori |
| 2007/0286881 A1 | 12/2007 | Burkinshsw |
| 2008/0027030 A1 | 1/2008 | Stogniew et al. |
| 2008/0064721 A1 | 3/2008 | Rohrs et al. |
| 2008/0066741 A1 | 3/2008 | LeMahieu et al. |
| 2008/0103564 A1 | 5/2008 | Burkinshaw et al. |
| 2008/0145405 A1 | 6/2008 | Kunzler et al. |
| 2008/0145419 A1 | 6/2008 | Gibson et al. |
| 2008/0152708 A1 | 6/2008 | Gibson et al. |
| 2008/0214649 A1 | 9/2008 | Yu et al. |
| 2008/0294261 A1 | 11/2008 | Pauza et al. |
| 2008/0311171 A1 | 12/2008 | Patel et al. |
| 2009/0010924 A1 | 1/2009 | Wu et al. |
| 2009/0048268 A1 | 2/2009 | Asotra et al. |
| 2009/0054994 A1 | 2/2009 | Rogan et al. |
| 2009/0123367 A1 | 5/2009 | Bookbinder et al. |
| 2009/0137606 A1 | 5/2009 | Cohen |
| 2009/0156504 A1 | 6/2009 | Siegel et al. |
| 2009/0181908 A1 | 7/2009 | Kaspar et al. |
| 2009/0186038 A1 | 7/2009 | Reed |
| 2009/0216183 A1 | 8/2009 | Minotti |
| 2009/0227564 A1 | 9/2009 | Sugamata |
| 2009/0280129 A1 | 11/2009 | Liu et al. |
| 2009/0298869 A1 | 12/2009 | Burnier et al. |
| 2009/0304648 A1 | 12/2009 | Owen |
| 2009/0311311 A1 | 12/2009 | Shantha et al. |
| 2009/0312706 A1 | 12/2009 | Shantha et al. |
| 2010/0008996 A1 | 1/2010 | Meinert |
| 2010/0022496 A1 | 1/2010 | Perovitch et al. |
| 2010/0029662 A1 | 2/2010 | Horn |
| 2010/0069402 A1 | 3/2010 | Melamed |
| 2011/0004164 A1 | 1/2011 | Du |
| 2011/0008325 A1 | 1/2011 | Pipkin et al. |
| 2012/0053563 A1 | 3/2012 | Du |

FOREIGN PATENT DOCUMENTS

| | | |
|---|---|---|
| EP | 1098870 B1 | 10/2005 |
| WO | 9800159 A1 | 1/1998 |
| WO | 9822130 A1 | 5/1998 |
| WO | 0006531 A2 | 2/2000 |
| WO | 0128555 A1 | 4/2001 |
| WO | 0247689 A2 | 6/2002 |
| WO | 02067938 A2 | 9/2002 |
| WO | 2004084865 A1 | 10/2004 |
| WO | 2006047427 | 5/2006 |
| WO | 2006047427 A1 | 5/2006 |
| WO | 2009/044141 A1 | 4/2009 |

OTHER PUBLICATIONS

Annals of Allergy, Asthma & Immunology; 85; pp. 525-531; (2000).
Banerji, et al.; "Diphenhydramine Versus Nonsedating Antihistamines for Acute Allergic Reactions: A Literature Review"; Allergy Astharn Proc 28; pp. 418-426; (2007).
Coyle, et al.; "The effect of Cetirizine on Antigen-Dependent Leucopenia in the Guinea-Pig"; Br. J. Pharmacol; 103 (2); pp. 1520-1524; (1991).
Desager et al.; "A Pharmacokinetic Evaluation of the Second-Generation H1-Receptor Antagonist Cetirizine i n Very Young Children"; Clin. Pharmacol. Ther.; 53(4); pp. 431-435; (1993).
Dux, et al.; "Possible Role of Histamine (H1-and H2-) Receptors in the Regulation of Meningeal Blood Flow"; Br. J. Pharmacol.; 137(6); pp. 874-880; (2002).
Epipen (epinephrine) Auto-Injector 0.3 mg; label; Meridian Medical Technologies, Inc.; Manufactured for Dey, L.P.; 7 pages; (Sep. 2008).
Hydroxyzine Description; American Regent Labortories, Inc.; 9 pages; Revised: Nov. 2006.
International Search Report and Written Opinion; International Application No. PCT/US10/40925; International Filing date Jul. 2, 2010; Applicant's File Reference 137173.00112; date of Mailing Aug. 30, 2010; 12 pages.
Jaber et al.; "Determination of Cetirizine Dihydrochloride, Related Impurities and Preservatives in Oral Solution and Tablet Dosage Forms Using HPLC"; J. Pharm. Biomed. Anal.; 36():341-350; (2004).
U.S. Appl. No. 12/829,857, filed Jul. 2, 2010, NonFinal Office Action of Mar. 15, 2012, 24 pages.
U.S. Appl. No. 12/704,089, filed Feb. 11, 2010; Non-final Office Action of Mar. 29, 2012; 12 pages.
Krause, Richard S.; "Anaphylaxis"; eMedicine.com, Updated: Oct. 6, 2008.
Lieberman; "The Use of Antihistamines in the Prevention and Treatment of Anaphylaxis and Anaphylactoid Reactions"; J. Allergy Clin. Immunol.; 86(4/2); pp. 684-686; (1990).
Linder et al.; "Hydroxyzine Hemolysis in Surgical Patients"; Anesthesia and Analgesia; 46(1); 6 pages; (1967).
Linzer, Jeffrey F. Sr.,; "Pediatric, Anaphylasix"; eMedicine.com; 9 pages; Updated: Jan. 10, 2008.
"Hydroxyzine"; 2006 Lippincott's Nursing Drug Guide; ed. Lippincott Williams & Wilkins; http://web.sqe.edu.om/med-Lib/MED_CD/E_CDs/Nursing%20Drug%20Guide/mg/hydroxyzine.htm; (2006).
"Metoclopramide Injection", Solution (archived drug label, Jun. 2006; available online at http://dailymed.nlm.nih.gov).
U.S. Appl. No. 12/704,089, filed Feb. 11, 2010, NonFinal Office Action of Aug. 5, 2011.
Pfizer Labs, Zyrtec; May 1, 2006, online drug review, retrieved Mar. 28, 2011, from pfizer.com/files/products/uspi_syrtec.pdf, 14 pages.
"Hydroxyzine (Atarax) Adverse Reactions"; RX-s.net Online pharmacy; http://rx-s.net/weblog/more/atarax_adverse_reactions/; last revised: Dec. 11, 2002.

(56) References Cited

OTHER PUBLICATIONS

Salzbert, et al.; "Anaphylaxis: When Seconds Count"; Emerg Med; 39(5):18; 7 pages; (2007).
Sampson, Hugh A.; "Anaphylaxis and Emergency Treatment"; Pediatrics; 111(6); pp. 1601-1608; (2004).
Sampson, et al.; "Symposium on the Definition and Management of Anaphylaxis: Summary Report"; J Allergy Clin Immunol; 115; pp. 584-591; (2005).
Shands "Drugs & Therapy Bulletin"; 15(6) 4 pages; (2001).
Tillement et al., "Compared Pharmacological Characteristics in Humans of Racemic Cetirizine and Levocetirizine, Two Histamine H1-Receptor Antagonists"; Biochemical Pharmacology; 66; No. 7; pp. 1123-1126; (2003).
Tokodi, Jr., et al.; "Massive Tissue Necrosis After Hydroxyzine Injection"; J. Am Osteopath Assoc; 95(10); p. 609; Abstract only; (1995).
Winbery, et al.; Clin Allergy Immunol; 17; pp. 287-317; Abstract only (2002).
Xyzal (levocetirizine dihydrochloride) 5 mg tablets; product label; UCB, Inc.; 9 pages; (2009).
Zyrtec-D 12 Hour (cetirizine hydrochloride 5 mg and pseudoephedrine hydrochloride 120 mg) Extended Release Tablets; product label; Pfizer Labs; Marketed by UCB Pharma, Inc.; 13 pages; Revised Aug. 2003.
EPO Search Report; Application No. PCT/US/2010040925; date of completion Oct. 17, 2012; 8 pages.
U.S. Appl. No. 13/238,453, filed Sep. 21, 2011 NonFinal Office Action Mailed Sep. 18, 2012.
Jones et al.; "Time-dependent Inhibition of Histamine-Induced Cutaneous Responses by Oral and Intramuscular Diphenhydramine and Oral Fexofenadine"; Annals of Allergy, Asthma & Immunology; 100; pp. 452-456; (2008).
U.S. Appl. No. 13/291,514, filed Nov. 8, 2011 NonFinal Office Action Mailed Aug. 31, 2012, 29 pages.
EP Application No. 10 794 820.0-1464; Jul. 30, 2013; Office Action received Aug. 8, 2013; 14 pages.
Ferdman, Ronald M.; "Urticaria and Angioedema"; Clin Ped Emerg Med; 8; pp. 72-80; (2007).
U.S. Appl. No. 13/644,290, filed Oct. 4, 2012; NonFinal Office Action Mailed Sep. 25, 2014 28 pages.

NON-SEDATING ANTIHISTAMINE INJECTION FORMULATIONS AND METHODS OF USE THEREOF

CROSS REFERENCE TO RELATED APPLICATION

This application is a continuation of U.S. application Ser. No. 12/704,089 filed on Feb. 11, 2010 now U.S. Pat. No. 8,263,581, which is a nonprovisional of U.S. Provisional Application Ser. Nos. 61/248,441 filed Oct. 3, 2009 and 61/222,951 filed Jul. 3, 2009, all which are hereby incorporated by reference in their entirety.

BACKGROUND

Acute allergic reaction including anaphylaxis, is a systemic, immediate hypersensitivity reaction caused by exposure to a specific antigen. The immune system activates immunoglobulin E (IgE), which reacts with effector cells (mast cells and basophils). These cells, in turn, release histamine, serotonin, leukotrienes, and prostaglandins, and induce a range of signs and symptoms, such as facial flushing, urticaria (hives), edema, pruritus, broncho-constriction, cough, cardiac arrhythmias, hypotension, nausea, vomiting, and diarrhea. Cutaneous manifestations are most common, with urticaria and angioedema present in 88% or more of patients experiencing acute allergic reactions. Swelling in the airway is the most life-threatening symptom, commonly causing dyspnea, wheezing, stridor, and upper airway obstruction from severe edema. Cardiovascular symptoms include dizziness, hypotension, and syncope related to third-spacing of intravascular fluid. Common gastrointestinal manifestations include nausea, vomiting, abdominal pains or cramps, and diarrhea. Although symptoms vary between acute allergy patients, onset generally occurs seconds to minutes after exposure to an antigen and requires prompt treatment.

The true incidence of acute allergic reactions including anaphylaxis is unknown, partly because of the lack of a precise definition of the syndrome. Some clinicians reserve the term anaphylaxis for the full-blown syndrome, while others use it to describe milder cases. Fatal anaphylaxis is relatively rare; milder forms occur much more frequently. The frequency of acute allergic reaction is increasing, and this has been attributed to the increased number of potential allergens to which people are exposed, such as increased varieties of food and medications. A recent review concluded that the lifetime prevalence of acute allergic reactions including anaphylaxis is ~5% of the population with higher prevalence in developed countries than developing countries.

Approximately 1 in 5000 exposures to a parenteral dose of a penicillin or cephalosporin antibiotic causes anaphylaxis. More than 100 deaths per year are reported in the United States due to antibiotic induced allergies. Fewer than 100 fatal reactions to Hymenoptera stings are reported each year in the United States but this is considered to be an underestimate. One to 2% of people receiving IV radiocontrast experience some sort of reaction. The majority of these reactions are minor, and fatalities are rare. Low molecular weight contrast causes fewer and less severe reactions. Narcotics also induce acute allergic reactions.

Acute allergic reactions occur in all age groups. Food allergies are more common in the young, whereas more drug reactions occur in adults, possibly due to greater exposure to medications, including narcotics, aspirin/NSAIDs, antibiotics, IV contrast media, anesthesia, muscle relaxants, etc. Although prior exposure is essential for the development of true anaphylaxis, reactions occur even when no documented prior exposure exists. Thus, patients may react to a first exposure to an antibiotic or insect sting. Elderly persons have the greatest risk of mortality from acute allergic reactions due to the presence of preexisting disease.

Emergency treatment includes airway protection, alpha-agonists, antihistamines, steroids, and beta agonists. Medications currently used in the treatment of acute allergic reactions include epinephrine, diphenhydramine injection, corticosteroids, albuterol, and glucagon. Epinephrine is the first-line drug to be given to a patient having an acute allergic reaction. An alpha-receptor agonist, epinephrine reverses hypotension. It also has beta-receptor activity, which dilates the airways, increases the force of myocardial contraction, and suppresses histamine and leukotriene release, reducing inflammatory responses. Diphenhydramine injection is the second—line drug to be given to a patient having an acute allergic reaction as an adjunct therapy to epinephrine for the relief of peripheral symptoms such as pruritus, engioedema, hives, erythema, etc.

What is needed are additional treatments for severe allergic reactions including anaphylaxis.

SUMMARY

In one aspect, a method of treating anaphylaxis or an acute allergic reaction comprises administering to an individual in need thereof an effective amount of an injectable composition comprising a non-sedating (also termed as $2^{nd}$ or $3^{rd}$ generation) H1 antihistamine wherein the H1 antihistamine comprises cetirizine, loratadine, levocetirizine, desloratadine, or fexofenadine.

In another aspect, the 90% confidence limits of a ratio of a logarithmic transformed geometric mean of $AUC_{0\text{-}INF}$ for the injectable formulation as described above to a logarithmic transformed geometric mean of $AUC_{0\text{-}INF}$ for a reference oral product of the non-sedating H1 antihistamine are 0.80 to 1.25; and/or wherein the 90% confidence limits of a ratio of a logarithmic transformed geometric mean of $AUC_{0\text{-}t}$ for the injectable formulation to a logarithmic transformed geometric mean of $AUC_{0\text{-}t}$ for the reference oral product of the non-sedating H1 antihistamine are 0.80 to 1.25.

In yet another aspect, the injectable formulation of the non-sedating antihistamine as described above has a 90% confidence interval around the difference in the reduction of at least one symptom of anaphylaxis or an acute allergic reaction to a reference injectable product, such as diphenhydramine injection, for the per protocol evaluable population, within about −30.00 to about +30.00, wherein the symptom is pruritus severity, pruritus duration, erythema, angioedema, number of urticaria areas, number of erythema areas, and/or wheezing.

In another aspect, the injectable formulation of the non-sedating antihistamine as described above is statistically superior ($p<0.05$) to a placebo in the reduction of at least one symptom of anaphylaxis or an acute allergic reaction, wherein the symptom is pruritus severity, pruritus duration, erythema, angioedema, urticaria areas, erythema areas, and/or wheezing.

In another aspect, an automatic injector designed to allow a user to self-administer a pre-measured dose of a non-sedating antihistamine composition subcutaneously or intramuscularly, comprises a housing comprising a chamber for the non-sedating antihistamine composition and a dispensing assembly in communication with the chamber, wherein the non-sedating antihistamine composition comprises an non-sedating antihistamine and a pH adjusting agent and has a pH of 3 to 9, wherein the non-sedating antihistamine comprises cetirizine, loratadine, levocetirizine, desloratadine, or fexofenadine.

In yet another aspect, a kit comprises the automatic injector comprising a non-sedating antihistamine composition as described above and a second automatic injector comprising a second housing comprising a second chamber for an epinephrine composition and a second dispensing assembly in communication with the second chamber.

DETAILED DESCRIPTION

Acute allergic reaction including anaphylaxis is an acute multi-system severe type I hypersensitivity reaction. Pseudoanaphylaxis does not involve an allergic reaction, but is due to direct mast cell degranulation. Both anaphylaxis and pseudoanaphylaxis result in an anaphylactoid reaction and treatment for both conditions is similar. The term anaphylaxis as used herein refers to both conditions unless otherwise specified. Clinical signs and symptoms of acute allergic reaction are given in Table 1:

TABLE 1

Clinical signs and symptoms of acute allergic reactions including anaphylaxis

Cutaneous/subcutaneous/mucosal tissue

Flushing, pruritus, hives (urticaria), angioedema, morbilliform rash, pilor erection
Pruritus of lips, tongue, and palate; edema of lips, tongue, and uvula
Periorbital pruritus, erythema and edema, conjunctival erythema, tearing
Respiratory Laryngeal: pruritus and tightness in the throat, dysphagia, dysphonia and hoarseness, dry staccato cough, stridor, sensation of pruritus in the external auditory canals
Lung: shortness of breath, dyspnea, chest tightness, deep cough and wheezing/bronchospasm (decreased peak expiratory flow)
Nose: pruritus, congestion, rhinorrhea, sneezing
Cardiovascular Hypotension
Feeling of faintness (near-syncope), syncope, altered mental status
Chest pain, dysrhythmia
Gastrointestinal Nausea, crampy abdominal pain, vomiting (stringy mucus), diarrhea
Other Uterine contractions in women, and aura of doom Disclosed herein are injection formulations of non-sedating antihistamines to be used, for example, in the hospital or acute care settings. In allergic reactions, an antigen interacts with and cross-links surface IgE antibodies on mast cells and basophils. Once the mast-cell-antibody-antigen complex is formed, a complicated series of events occurs that eventually leads to mast cell degranulation and the release of histamine and other chemical mediators from the mast cell or basophil. After its release, histamine can react with local or widespread tissues through histamine receptors. Histamine receptor sites, histamine-1 ($H_1$), and histamine-2 ($H_2$) have a role in acute allergic reactions/anaphylaxis. Acting on $H_1$ receptors, histamine produces pruritus, vasodilation, hypotension, flushing, headache, tachycardia, bronchoconstriction, and increased vascular permeability. Targeting $H_2$-receptor sites, histamine causes increased stomach acid production, nausea, and flushing.

Symptoms of acute allergic reactions include pruritus, erythema, angioedema, urticaria, urticaria areas, erythema areas, wheezing, and etc. Exemplary patient populations for study include patients coming to emergency rooms or allergy clinics, patients with food allergies (peanuts, other nuts, sea food, etc), patients with exercise induced allergies, patients allergic to insects stings, patients with poison Ivy induced allergies, etc. Additional patients include those already in the hospital experiencing drug induced allergies to: antibiotics, IV contrast media, anesthesia, aspirin/NSAIDs, opioids, chemotherapy agents, muscle relaxants, latex gloves, blood materials, etc.

In one aspect, a clinical endpoint bioequivalence study to compare the efficacy of a non-sedating antihistamine or second or third generation antihistamine injection to diphenhydramine injection is performed. In another embodiment, the efficacy of a non-sedating antihistamine or second or third generation antihistamine injection is compared to placebo.

Pruritus is a condition involving localized or general itching that is a common and distressing symptom in a variety of diseases, especially in an allergic reaction. Although usually occurring in the skin, pruritus can also occur in non-cutaneous sites such as mucous membranes. Erythema is redness of the skin, caused by congestion of the capillaries in the lower layers of the skin. The primary efficacy endpoints included the pruritus severity score and the erythema severity score (scored on a 0=absent, 1=mild, 2=moderate, to 3=severe scale, at 0.5 increments), and the reduction of the scores following treatment. For clinical trials, patients with "score 1-3" (mild to severe) will be recruited.

The primary efficacy end points are the difference between the treatment disclosed herein and the treatment of placebo in the mean change from the baseline of the average of the pruritus severity score and the erythema severity score. The study will be designed to give a 90% power to detect a 0.5 unit mean difference for the primary efficacy endpoint at a two-sided alpha-level of 0.05.

In addition, the duration of pruritus as an efficacy end point that can be measured. Duration of pruritus is categorized as follows: 3 if >6 hours/24 hr, 2 if 1 to 6 hours/24 hr, 1 if less than 1 hour/24 hr, and 0 if no pruritus. The study will be designed to give a 90% power to detect a 0.5 unit mean reduction for the primary efficacy endpoint at a two-sided alpha-level of 0.05.

Angioedema is an uncomfortable and disfiguring type of temporary swelling especially in the lips and other parts of the mouth and throat, the eyelids, the genitals, and the hand and feet. Angioedema is life-threatening if swelling in your mouth or throat makes it difficult for you to breathe. Less often the sheer amount of swelling means that so much fluid has moved out of the blood circulation that blood pressure drops dangerously. The primary efficacy endpoints for angioedema include the angioedema severity score (scored on a 0=absent, 1=mild, 2=moderate, to 3=severe scale, at 0.5 increments), and the reduction of the score following treatment.

Wheezing is a high-pitched whistling sound produced by air flowing through narrowed breathing tubes, especially the smaller ones deep in the lung. The primary efficacy endpoints include the wheezing severity score (scored on a 0=absent, 1=mild, 2=moderate, to 3=severe scale, at 0.5 increments), and the reduction of the score following treatment.

Exemplary clinical studies include a randomized, double-blind, active and placebo—controlled trial of about 300 patients over the age of 12 with acute allergic syndromes. About 100 patients will be randomly assigned to each of the 3 treatments including a non-sedating antihistamine injection as disclosed herein, a diphenhydramine injection, or a placebo injection, all via intravenous, intramuscular or subcutaneous administration. Patients will be recruited at multiple centers, from emergency departments at urban hospitals and allergy clinics throughout the country. The primary endpoints will be the reduction of pruritus severity score, pruritus duration, erythema, angioedema, wheezing, number of urticaria areas, and/or number of erythema areas, at 2-4 hours after protocol treatment. Symptom scores will be also assessed at baseline.

A broad definition of allergic syndromes to approximate real-life emergency department (ED) approaches will be used to assess the patients with various symptoms and signs. Patients over the age of 12 will be considered for recruitment from the ED if they have the following syndromes after an ingested food or ingested, inhaled, or injected drug, after in contact with latex or bee stings: acute urticaria (score 1 and above), acute angioedema (score 1 and above), wheezing (score 1 and above), and acute pruritic rash (score 1 and above). These manifestations should have been present for no greater than 12 hours from the time of alleged allergen exposure. Pregnant patients will be excluded. Recruited patients will be randomly assigned to treatment with either 10 mg of cetirizine injection (the test product group, i.e. product of present disclosure), diphenhydramine 50 mg injection (the comparator or active control group) or placebo injection (placebo control group)

Each treatment designation will be blinded based on the randomization code. The physician who is unaware of the treatment content will administer the contents by means of intravenous (or intramuscular, or subcutaneous, depending on protocol requirement) injection to the subject. Supplemental medications, such as epinephrine, corticosteroids, bronchodilators, and additional doses of antihistamine may be administered at the discretion of the study physicians as a rescue procedure. Patients may also receive supplemental oxygen and intravenous fluids at the discretion of the study physicians as a rescue procedure. Patients will have heart rate, blood pressure, physical findings, side effects, and symptoms assessed at baseline, 1 hour, 2 hours and 4 hours relative to experimental treatment. Baseline temperatures will be also recorded. Clinical recording will include the presence and extent or severity scores of urticaria and erythema, angioedema, wheezing, pruritus, number of urticaria areas, number of erythema areas, abdominal distention or tenderness, and abdominal hyperactive bowel sounds. Historical features, physical findings (including heart rates, blood pressure, and respiratory rates), and treatments will be recorded on a study-specific data input form. The extent of involvement with urticaria and erythema will be assessed by using a check-off cartoon of body areas (similar to that used to assess burn area extent) printed on the data input sheet. Symptom scores will be assessed at baseline, 1 hour, and 2, or 4 hours by using a preprinted form with none (score 0), mild (score 1), moderate (score 2), and severe (score 3) check-off categories.

The primary variables of interest will be resolution or reduction of urticaria, angioedema, erythema, pruritus, wheezing, number of urticaria areas, and number of erythema areas. Changes in heart rates, respiratory rates, blood pressure, and symptoms will also be examined. The final disposition of the patient will be noted (admission, discharge, or leaving against medical advice). The study will be approved by the institutional review board, and informed written consent will be obtained from all patients.

Statistical assessment will be using bivariate $x^2$ analysis and analysis of variance or covariance (ANCOVA), multivariate logistic regression. Covariates will be included in some multivariate models. Analyses will be performed by using the SAS software. Certain statistical values are expressed with 90% confidence intervals (CIs).

The above clinical trials may be split into two separate studies. One study will be an active controlled study comparing the invention injectable product with diphenhydramine injection. The other will be a placebo controlled study comparing the invention injectable product with a placebo.

In addition, pediatric studies will be conducted on patients younger than the age of 12 with similar study design and lower drug dosage.

Prompt treatment with antihistamines is highly recommended to alleviate the symptoms of acute allergic reactions. Antihistamines are helpful in reducing histamine-mediated vasodilation and secondary edema. Commonly used drugs such as diphenhydramine injection provide $H_1$ blockade. Diphenhydramine reduces vasodilation in small blood vessels in the nose, eyes, and airways and provide some anticholinergic effects toward drying secretions. Diphenhydramine (1 to 2 mg/kg, up to a maximum of 50 mg, given IV or IM) is the drug of choice when treating acute allergic reactions. Concomitant administration of an $H_2$ agonist such as ranitidine (1 mg/kg IV) or cimetidine (4 mg/kg IV) is also of value to provide antihistaminic effect.

Currently, the only antihistamine injection existing on the market is diphenhydramine injection, a first generation antihistamine, with known side effects of cardio toxicity (QT prolongation), severe sedation, anti-cholinergic effect, potential of drug/drug interaction, and short acting which requires 3-4 doses a day. Cardio toxicity presents a huge safety concern, and the sedation side effect causes significantly inconvenience and discomfort for patients. The sedating side effect presents a safety concern when patients have to drive home themselves after being discharged from the emergency room. The sedating side effect also interferes with neurological exams for patients who are in need such exams in the hospital. Patients with allergic reactions to opioids are treated with diphenhydramine injections. This causes a dangerous additive effect in sedation. Diphenhydramine's QT prolongation is potentially life threatening and could lead to hospital admission. Sometimes severe allergic patients come to the ER and already took a few diphenhydramine tablets. ER doctors then put the patients on injection diphenhydramine as a standard procedure. This accumulated diphenhydramine concentration could cause cardiac arrest leading to hospital admission. QT prolongation is worsened by drug/drug interaction. In ICUs, diphenhydramine injection is frequently used as a preventive measure to desensitize antibiotics (antibiotics have a high incidence for drug induced allergic shock). In ICUs, patients are normally on multiple medications, and the potential drug/drug interaction and liver enzyme P450 inhibition leading to cardiac arrest due to QT prolongation is extremely dangerous. Diphenhydramine injection is commonly used together with blood transfusion to prevent allergic reactions to blood or plasma. Clearly sedation is unwanted. Diphenhydramine injection is often used to treat anesthesia induced allergies in the operating room. It takes longer for patients to awake from the anesthesia when diphenhydramine injection is co-used.

Therefore there is a great advantage and unmet medical need for a non-sedating antihistamine injection with longer duration of action, and without QT prolongation.

In one embodiment, the present disclosure includes injectable formulations of second and third generation antihistamines, or non-sedating antihistamines, via intravenous, intramuscular, or subcutaneous administration to provide an immediate onset of action. Such second and third generation antihistamines are commercially available as oral dosage forms as shown in the following table.

TABLE 2

Second and third generation antihistamines

Currently marketed dosage form

| | |
|---|---|
| Second generation antihistamines | |
| cetirizine | 10 mg tablet, once daily for adults over 6<br>5 mg chewable, once daily for children under 6<br>$AUC_{0-24}$ = about 4023 ng · hr/mL for adult dose of 10 mg; (range: about 2500 to about 5500 ng · hr/mL)<br>$AUC_{0-INF}$ = about 4638 ng · hr/mL, for adult dose of 10 mg; (range: about 3000 to about 6200 ng · hr/mL) |
| loratidine | 10 mg tablet every 12 hours for adults over 6<br>5 mg chewable every 12 hours for children 2-6<br>$AUC_{0-24}$ = about 7.36 ng · hr/mL (fasting)<br>$AUC_{0-INF}$ = about 7.90 ng · hr/mL (fasting)<br>$AUC_{0-24}$ = about 10.3 ng · hr/mL (fed)<br>$AUC_{0-INF}$ = about 11.1 ng · hr/mL (fed) |
| Third generation antihistamines | |
| fexofenadine | 60 mg tablet twice daily or 180 mg tablet once daily for adults over 12<br>30 mg tablet once daily for children 6-11<br>$AUC_{0\text{-}inf\,(60\,mg)}$ = about 958 ng · hr/mL<br>$AUC_{0\text{-}inf\,(180\,mg)}$ = about 3397 ng · hr/mL<br>$AUC_{0\text{-}INF\,(240\,mg)}$ = about 6571 ng · hr/mL |
| levocetirizine | 5 mg tablet, once daily for adults over 12<br>2.5 mg tablet once daily for children 6-11<br>1.25 mg (½ teaspoon oral solution) once daily for children 6 months to 5 years<br>$AUC_{0-24}$ = about 3469 ng · hr/mL; (range: about 1500 to about 5000 ng · hr/mL)<br>$AUC_{0-INF}$ = about 3998 ng · hr/mL; (range: about 2000 to about 5500 ng · hr/mL) |
| desloratadine | 5 mg tablet once daily for adults over 12<br>1 teaspoonful (2.5 mg in 5 mL) once daily for children 6 to 11<br>½ teaspoonful (1.25 mg in 2.5 mL) once daily for children 12 months to 5 years<br>AUCss = about 56.9 ng·hr/mL<br>$AUC_{0-24}$ (single dose) = about 34.2 ng · hr/mL<br>AUC (single dose) 0-inf = about 35.6 ng/hr/mL |

Additional non-sedating antihistamines include desdiphenhydramine, epinastine, azelastine, Acrivastine, Ebastine, carbastine, levocarbastine, Mizolastine, and Rupatadine.

Parenteral injectable formulations may be in unit dose form in ampoules, small volume parenteral (SVP) vials, large volume parenterals (SVP), pre-filled syringes, small volume infusion or in multi-dose containers with an added preservative. The compositions may take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and may contain formulatory agents such as preserving, wetting, buffering, emulsifying or suspending, stabilizing and/or dispersing agents. Alternatively, the active ingredient may be in powder form, obtained by aseptic isolation of sterile solid or by lyophilization from solution for constitution before use with a suitable vehicle, e.g., sterile, pyrogen-free water.

Parenteral injectable formulations are typically aqueous solutions which may contain excipients such as salts, carbohydrates and buffering agents (preferably at a pH of from 3 to 9.5), but, for some applications, they may be more suitably formulated as a sterile non-aqueous solution or as a dried form to be used in conjunction with a suitable vehicle such as sterile, pyrogen-free water.

In one embodiment, the injectable compositions contain a solution of one or more non-sedating antihistamines in an aqueous solvent combined with a buffer or pH adjusting agents having a pH of 3 to 9. The composition optionally contains at least one isotonicity agent. A water-insoluble inert gas may be carefully bubbled through the aqueous solvent to remove oxygen from the medium. Optionally the compositions contain at least one preservative and/or at least one solubility enhancing agent and/or at least one stabilizing agent.

In one embodiment, the non-sedating H1 antihistamine is cetirizine or a salt thereof. In another embodiment, the quantity of cetirizine or salt thereof in the injection formulation is 1-100 mg per milliliter of liquid, preferably 1.5-50 mg, more preferably 2-25 mg per milliliter of liquid.

In another embodiment, the non-sedating H1 antihistamines is fexofenadine or a salt thereof. In yet another embodiment, the quantity of fexofenadine or salt thereof in the injection formulation is 1-200 mg per milliliter of liquid, preferably 1.5-180 mg, preferably 2-90 mg, more preferably 2.5-70 mg per milliliter of liquid.

In another embodiment, the injectable composition optionally comprises at least one H2 antihistamine, specifically ranitidine and cimetidine, more specifically ranitidine. Concomitant administration of an H2 agonist such as ranitidine (1 mg/kg IV) or cimetidine (4 mg/kg IV) may be of value to provide antihistaminic effect.

Due to the fast onset of acute allergic reactions including anaphylaxis, often patients do not have sufficient time to reach medical care facilities for treatment. In this life and death situation, it is important that patients administer medications to themselves immediately.

Accordingly, there is a need in the art to develop injectable formulations and optionally self operated and ready to use auto injector products, needle or needleless, providing a rapid delivery of the injectable non-sedating antihistamine formulation.

An automatic injector or auto-injector is a device designed to allow a user to self-administer a pre-measured dose of a medicament composition subcutaneously or intramuscularly, usually in an emergency situation. A typical auto-injector has a housing, inside of which is a cartridge. The cartridge has one or several chambers containing medicament compositions or components thereof and is in communication with a dispensing assembly such as needle assembly. The cartridge can hold either a pre-mixed liquid medicament or a solid medicament and a liquid that are mixed prior to injection. The housing carries an actuation assembly with a stored energy source, for example, a compressed spring. Activation of the actuation assembly causes a sequence of movements, whereby the needle extends from the auto-injector into the user so that the medicament compound is then forced through the needle and into the user. After delivery of the dose of medicament into the injection site, the needle remains in an extended position or in a hidden position. If the auto-injector is of the type designed to carry plural components of the medicament composition in separate, sealed compartments, structure may be included that forces the components to mix when the actuation assembly is activated.

Autoinjectors for antihistamine administration do not exist. Advantages of the use of auto-injectors to dispense non-sedating (second and third generation) antihistamines for the treatment of severe allergic reactions include availability for emergency treatment, precise dosing, portability, readiness for use, rapid intramuscular or subcutaneous administration, administration through clothing and protective wear, and rapid self-administration. The advantages of this invention also include its non-cardiotoxicity (no QT prolongation), and non-sedating. Unlike the current highly sedating diphenhydramine injections, the non-sedating feature of this invention allows patients to be alert enough to drive to the hospital or emergency care facility after they self administer the non-sedating antihistamine injection via an auto injector.

In another embodiment, a kit comprises the automatic injector comprising a non-sedating antihistamine composition as described above, and a second automatic injector comprising a second housing comprising a second chamber for an epinephrine composition and a second dispensing assembly in communication with the second chamber.

In one embodiment, disclosed herein is an injectable second or third generation antihistamine (non-sedating antihistamine) formulation. Also disclosed are methods of treating an acute allergic reaction comprising administering to an individual in need thereof an effective amount of an injectable composition comprising a second or third generation antihistamine (or non-sedating antihistamine). In specific embodiments, the antihistamine is not diphenhydramine. In other embodiments, the non-sedating antihistamine is selected from cetirizine, loratadine, levocetirizine, desloratadine, and fexofenadine, des-diphenhydramine, epinastine, azelastine, Acrivastine, Ebastine, carbastine, levocarbastine, Mizolastine, and Rupatadine.

In one embodiment, the injectable formulation further comprises at least one H2 receptor antagonist, such as ranitidine or cimetidine. In another embodiment, the injectable formulation further comprises epinephrine. In yet another embodiment, the injectable formulation further comprises at least one steroid, such as methylprednisolone or prednisolone.

In one embodiment, disclosed herein are methods of treating an acute allergic reaction comprising administering to an individual in need thereof an effective amount of an injectable composition comprising a second or third generation antihistamine (or non-sedating antihistamine), wherein the injectable composition is bioequivalent to an oral formulation of the $2^{nd}$ or $3^{rd}$ generation antihistamine.

| Non-sedating Antihistamine | Oral product | Dosage range of injectable formulation |
|---|---|---|
| Cetirizine | 10 mg tablet<br>10 mg chewable tablet<br>10 mg capsule<br>5 mg tablet<br>5 mg/5 mL syrup | about 2 mg to about 10 mg |
| Loratadine | 10 mg tablet<br>10 mg capsule<br>5 mg tablet<br>5 mg chewable tablet<br>0.5 mg/mL syrup<br>1 mg/mL suspension<br>1 mg/mL syrup | about 1 mg to about 10 mg |
| Fexofenadine | 180 mg tablet/capsule<br>60 mg tablet<br>30 mg tablet<br>30 mg/5 mL suspension | about 5 mg to about 180 mg |
| Levocetirizine | 5 mg tablet<br>2.5 mg tablet<br>2.5 mg/5 mL syrup | about 1 mg to about 5 mg |
| Desloratadine | 5 mg tablet<br>2.5 mg/5 mL syrup | about 1 mg to about 5 mg |

As used herein, the term equivalent to an oral product means that the 90% confidence limits of a ratio of a logarithmic transformed geometric mean of $AUC_{0\text{-}INF}$ and/or $AUC_{0\text{-}t}$ for the injectable formulation to a logarithmic transformed geometric mean of $AUC_{0\text{-}INF}$ and/or $AUC_{0\text{-}t}$ for the reference oral product are about 0.80 to about 1.25, specifically 0.80 to 1.25. "AUC" is the area under the curve of a graph of the measured concentration of an active agent (typically plasma concentration) vs. time, measured from one time point to another time point. For example $AUC_{0\text{-}t}$ is the area under the curve of plasma concentration versus time from time 0 to time t, the last blood draw time point. The $AUC_{0\text{-}\infty}$ or $AUC_{0\text{-}INF}$ is the calculated area under the curve of plasma concentration versus time from time 0 to time infinity by extrapolation. In one embodiment, the $AUC_{0\text{-}INF}$ and/or $AUC_{0\text{-}t}$ are given in Table 2. In another embodiment, the $AUC_{INF}$ and/or $AUC_{0\text{-}t}$ for the injectable formulation and the reference oral dosage form are given determined in a reference-controlled study.

In one embodiment, disclosed herein are methods of treating an acute allergic reaction including anaphylaxis comprising administering to an individual in need thereof an effective amount of an injectable composition comprising a second or third generation antihistamine (or non-sedating antihistamine), wherein the injectable composition is therapeutically equivalent to a reference diphenhydramine injectable formulation. In one embodiment, the reference diphenhydramine injectable formulation is a 50 mg/mL solution, and the dose is about 12.5-150 mg dose. Diphenhydramine injection is commercially available from Pfizer as Benadryl® Injection. Many generic versions of diphenhydramine injections are also available on the market. Therapeutic equivalence can be determined in a reference-controlled study using a diphenhydramine injectable formulation as the reference.

As used herein, therapeutically equivalent to a reference diphenhydramine injectable formulation means that the test formulation has a 90% confidence interval around the difference in the reduction of at least one symptom of an acute allergic reaction including anaphylaxis of the test drug to the reference drug, for the per protocol evaluable population, within about −30.00 to about +30.00. In specific embodiments, the symptoms of anaphylaxis or an acute allergic reaction are, pruritus severity, pruritus duration, erythema, angioedema and/or wheezing reduction, and urticaria areas or erythema areas.

Predicted results for clinical equivalence are presented in Table 3:

| Treatment | N | Baseline | On Treatment adjusted mean | Difference from Placebo | 90% CI (−30.00, +30.00) |
|---|---|---|---|---|---|
| Pruritus severity score reduction | | | | | |
| Cetirizine 10 mg injection | About 100 | About 2.80 | About 1.70 | +0.05 | About (−3.00, 8.00) |
| Diphenhydramine 50 mg injection | About 100 | About 2.75 | About 1.65 | | |

-continued

| Treatment | N | Baseline | On Treatment adjusted mean | Difference from Placebo | 90% CI (−30.00, +30.00) |
|---|---|---|---|---|---|
| Pruritus duration reduction |||||| 
| Cetirizine 10 mg injection | About 100 | | About 1.00 hr | −0.50 hr | About (−8.50, 3.50) |
| Diphenhydramine 50 mg injection | About 100 | | About 1.50 hr | | |
| Erythema Reduction |||||| 
| Cetirizine 10 mg injection | About 100 | About 2.50 | About 1.0 | 0.00 | About (−10.00, 10.00) |
| Diphenhydramine 50 mg injection | About 100 | About 2.55 | About 1.0 | | |
| Angioedema Reduction |||||| 
| Cetirizine 10 mg injection | About 100 | About 2.50 | About 1.0 | −0.25 | About (−10.00, 8.00) |
| Diphenhydramine 50 mg injection | About 100 | About 2.45 | About 1.25 | | |
| Wheezing reduction |||||| 
| Cetirizine 10 mg injection | About 100 | About 2.45 | About 1.40 | +0.40 | About (−0.20, 15.00) |
| Diphenhydramine 50 mg injection | About 100 | About 2.55 | About 1.00 | | |
| Number of urticaria areas |||||| 
| Cetirizine 10 mg injection | About 100 | About 4.2 | About 1.0 | −0.20 | About (−10.00, 8.00) |
| Diphenhydramine 50 mg injection | About 100 | About 4.0 | About 1.20 | | |
| Number of erythema areas |||||| 
| Cetirizine 10 mg injection | About 100 | About 7.0 | About 1.0 | −1.0 | About (−15.00, 10.00) |
| Diphenhydramine 50 mg injection | About 100 | About 7.2 | About 2.0 | | |

Expected results for effectiveness comparing to placebo are presented in Table 4:

| Treatment | N | Baseline | On Treatment adjusted mean | Difference from Placebo | P-value |
|---|---|---|---|---|---|
| Pruritus severity score reduction |||||| 
| Cetirizine 10 mg injection | About 100 | About 1.80 | About 2.80 | −0.70 | <0.05 |
| Placebo injection | About 100 | About 2.75 | About 2.50 | | |
| Pruritus duration reduction |||||| 
| Cetirizine 10 mg injection | About 100 | | About 1.50 hr | −2.5 hr | <0.05 |
| Placebo injection | About 100 | | About 4.00 hr | | |
| Erythema Reduction |||||| 
| Cetirizine 10 mg injection | About 100 | About 2.50 | About 1.0 | −1.15 | <0.05 |
| Placebo injection | About 100 | About 2.55 | About 2.15 | | |
| Angioedema Reduction |||||| 
| Cetirizine 10 mg injection | About 100 | About 2.50 | About 1.0 | −1.25 | <0.05 |
| Placebo injection | About 100 | About 2.45 | About 2.25 | | |
| Wheezing reduction |||||| 
| Cetirizine 10 mg injection | About 100 | About 2.45 | About 1.40 | −0.75 | <0.05 |
| Placebo injection | About 100 | About 2.55 | About 2.15 | | |
| Number of urticaria areas |||||| 
| Cetirizine 10 mg injection | About 100 | About 4.2 | About 1.0 | −2.8 | <0.05 |
| Placebo injection | About 100 | About 4.0 | About 3.8 | | |
| Number of erythema areas |||||| 
| Cetirizine 10 mg injection | About 100 | About 6.0 | About 1.0 | −4.0 | <0.05 |
| Placebo injection | About 100 | About 6.2 | About 5.0 | | |

In one embodiment, disclosed herein are methods of treating an acute allergic reaction including anaphylaxis comprising administering to an individual in need thereof an effective amount of an injectable composition comprising a second or third generation antihistamine, the non-sedating antihistamine, wherein the injectable composition is therapeutically effective compared to placebo. As used herein, a placebo is an inactive pill, liquid, or powder that has no treatment value. In clinical trials, experimental treatments are often compared with placebos to assess the treatment's effectiveness. A placebo-controlled study is a method of investigation of drugs in which an inactive substance (the placebo) is given to one group of participants, while the drug being tested is given to another group. The results obtained in the two groups are then compared to see if the investigational treatment is more effective in treating the condition.

As used herein, therapeutically effective compared to placebo means that the treatment of this invention is statistically superior (p<0.05) to a placebo in the reduction of at least one symptom of anaphylaxis or an acute allergic reaction, wherein the symptom is pruritus severity, pruritus duration, erythema, angioedema, urticaria areas, erythema areas, and/or wheezing.

The methods described herein optionally further comprise administering a second active agent as well as the second or third generation antihistamine. In one embodiment, the second active agent is an H2 receptor antagonist, such as ranitidine or cimetidine. In another embodiment, the second active agent is epinephrine. In yet another embodiment, the second active agent comprises at least one steroid, such as methylprednisolone or prednisolone. In one embodiment, the methods disclosed herein further comprise administering a second active agent comprising ranitidine, cimetidine, epinephrine, methylprednisolone, prednisolone, or a combination thereof.

The terms "a" and "an" do not denote a limitation of quantity, but rather denote the presence of at least one of the referenced item. The term "or" means "and/or." The terms "comprising," "having," "including," and "containing" are to be construed as open-ended terms (i.e., meaning "including, but not limited to"). Unless defined otherwise, technical and scientific terms used herein have the same meaning as is commonly understood by one of skill in the art to which this invention belongs. The endpoints of all ranges directed to the same component or property are inclusive and independently combinable.

The term "non-sedating antihistamines" represent the $2^{nd}$ and/or $3^{rd}$ generation antihistamines that are truly non-sedating and that are less-sedating than diphenhydramine.

The term "antihistamine" can also be expressed as "antagonist of the H1 receptor" or "H1 antihistamine".

The term "Therapeutic equivalence" can also be expressed as "clinical equivalence", "clinically bioequivalent", or "clinical endpoint bioequivalence".

The term "equivalent" can also be expressed as "bioequivalent".

"Acute allergic reaction" means an allergic condition of the immediate type, severe allergies/anaphylaxis, or severe allergic reaction such as allergic reactions to blood or plasma, to food, to medications, or to other allergy inducing materials.

Embodiments of this invention are described herein, including the best mode known to the inventors for carrying out the invention. Variations of those preferred embodiments would become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating acute urticaria or angioedema associated with an acute allergic reaction comprising administering to an individual in an emergency situation an effective amount of an injectable composition comprising racemic cetirizine or a salt thereof,
wherein the injectable composition is a sterile parenteral solution comprising 1 to 100 mg of cetirizine per milliliter of solution.

2. The method of claim 1, wherein treating comprises treating acute urticaria.

3. The method of claim 1, wherein treating comprises treating angioedema.

4. The method of claim 1, wherein the acute allergic reaction is anaphylaxis.

5. The method of claim 1, wherein the 90% confidence limits of a ratio of a logarithmic transformed geometric mean of $AUC_{0-INF}$ for the injectable composition to a logarithmic transformed geometric mean of $AUC_{0-INF}$ for a reference oral product of racemic cetirizine are 0.80 to 1.25.

6. The method of claim 1, wherein the injectable composition further comprises a second active agent comprising ranitidine, cimetidine, epinephrine, methylprednisolone, prednisolone, or a combination thereof.

7. The method of claim 2, wherein the injectable composition of cetirizine has a 90% confidence interval around the difference in the reduction of at least one symptom of acute urticaria to a reference injectable formulation, for the per protocol evaluable population, within about −30.00 to about +30.00, wherein the symptom is pruritus, number of urticaria areas, or urticaria areas.

8. The method of claim 7, wherein the reference injectable formulation is a 12.5-150 mg dose of a 50 mg/mL diphenydramine injectable formulation.

9. The method of claim 3, wherein the injectable composition of cetirizine has a 90% confidence interval around the difference in the reduction of at least one symptom of angioedema to a reference injectable formulation, for the per protocol evaluable population, within about −30.00 to about +30.00.

10. The method of claim 9, wherein the reference injectable formulation is a 12.5-150 mg dose of a 50 mg/mL diphenydramine injectable formulation.

11. The method of claim 2, wherein the injectable composition of the non-sedating antihistamine is statistically superior (p<0.05) to a placebo in the reduction of at least one symptom of acute urticaria, wherein the symptom is pruritus, number of urticaria areas, or urticaria areas.

12. The method of claim 3, wherein the injectable composition of the non-sedating antihistamine is statistically superior (p<0.05) to a placebo in the reduction of at least one symptom of angioedema.

13. The method of claim 1, wherein administering is intravenous injection.

14. The method of claim 1, wherein administering is intramuscular injection.

15. The method of claim 1, wherein the injectable composition is an aqueous solution.

16. The method of claim 1, wherein the injectable composition comprises 1.5 to 50 mg of cetirizine per milliliter of solution.

17. The method of claim 1, wherein the injectable composition comprises 2 to 25 mg of cetirizine per milliliter of solution.

18. The method of claim 1, wherein 2 to 10 mg of cetirizine are administered.

* * * * *